US008755574B2

(12) United States Patent
Declerck et al.

(10) Patent No.: US 8,755,574 B2
(45) Date of Patent: Jun. 17, 2014

(54) METHOD AND APPARATUS FOR CALIBRATING MEDICAL IMAGE DATA

(75) Inventors: Jerome Declerck, Oxford (GB); Matthew David Kelly, Botley (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 622 days.

(21) Appl. No.: 12/760,639

(22) Filed: Apr. 15, 2010

(65) Prior Publication Data

US 2010/0290680 A1 Nov. 18, 2010

(30) Foreign Application Priority Data

Apr. 15, 2009 (GB) .................................. 0906463.5

(51) Int. Cl.
*G06K 9/00* (2006.01)
(52) U.S. Cl.
USPC ....................................................... 382/128
(58) Field of Classification Search
USPC ................ 382/128–132, 207; 250/252.1
See application file for complete search history.

(56) References Cited

U.S. PATENT DOCUMENTS

| 2005/0157848 | A1* | 7/2005 | Miyauchi et al. | 378/207 |
| 2007/0019846 | A1* | 1/2007 | Bullitt et al. | 382/128 |
| 2008/0085041 | A1* | 4/2008 | Breeuwer | 382/128 |
| 2009/0127451 | A1* | 5/2009 | Watson et al. | 250/252.1 |
| 2009/0268876 | A1* | 10/2009 | Crucs et al. | 378/207 |
| 2009/0285357 | A1* | 11/2009 | Khamene et al. | 378/20 |
| 2010/0290680 | A1* | 11/2010 | Declerck et al. | 382/128 |

OTHER PUBLICATIONS

Zimny et al., "Analysis of FDG uptake with hybrid PET using standardised uptake values", European Journal of Nuclear Medicine, vol. 28, No. 5, May 2001.*
Geworski et al., "Recovery correction for quantitation in emission tomography: a feasibility study", European Journal of Nuclear Medicine, vol. 27, No. 2, Feb. 2000.*
Soret et al., Partial-volume effect in PET tumor imaging. J Nucl Med. Jun. 2007;48(6):932-45. Epub May 15, 2007.*
Hickeson et al., Use of a corrected standardized uptake value based on the lesion size on CT permits accurate characterization of lung nodules on FDG-PET. Eur J Nucl Med Mol Imaging. Dec. 2002;29(12):1639-47. Epub Oct. 2, 2002.*
Rousset et al., Partial Volume Correction Strategies in PET, PET Clinics. vol. 2, Issue 2, Apr. 2007, pp. 235-249.*
"Measurement of Clinical and Subclinical Tumour Response Using [18F]-fluorodeoxyglucose and Positron Emission Tomography: Review and 1999 EORTC Recommendations," Young et al., European Journal of Cancer, vol. 15, No. 13, pp. (1999) 1773-1782.

(Continued)

*Primary Examiner* — Elaine Gort
*Assistant Examiner* — Jonathan K Ng
(74) *Attorney, Agent, or Firm* — Schiff Hardin LLP

(57) ABSTRACT

In a method and apparatus for calibrating image data from a given medical imaging protocol, reference image data is obtained from a scan of a reference object using the medical imaging protocol, and the obtained reference image data of the reference object is compared to standard reference image data for the reference object. The obtained reference image data is then modified to reduce an error between the obtained reference image data and the standard reference image data. Subject image data id then obtained from a scan of a subject using the medical imaging protocol, and modified based on the modified reference image data. A value of a variable is obtained from the modified subject image data, for display with unmodified subject image data.

16 Claims, 3 Drawing Sheets

(56) References Cited

OTHER PUBLICATIONS

"Consensus Recommendations for the Use of 18F-FDG PET as an Indicator of Therapeutic Response in Patients in National Cancer Institute Trials," Shankar et al., Journal of Nuclear Medicine, vol. 47, No. 6 (2006) pp. 1059-1966.

"Procedure Guideline for Tumor Imaging with 18F-FDG PET/CT 1.0*," Delbeke et al., Journal of Nuclear Medicine, vol. 47, No. 5 (2006) pp. 885-895.

"Monitoring Cancer Treatment with PET/CT: Does It Make a Difference?," Weber et al., Journal of Nuclear Medicine, vol. 48, No. 1 (Suppl.) (2007) pp. 36S-44S.

"Standards for PET Image Acquisition and Quantitative Data Analysis," Boellaard, The Journal of Nuclear Medicine, vol. 50, No. 5, (Suppl) (2009) pp. 11S-20S.

"Standard Uptake Values in Whole-Body FDG PET: Effects of Acquisition and Processing Parameters," Ivanovic et al., IEEE Nuclear Science Symposium Conference Record (2003) pp. 2813-2816.

* cited by examiner

METHOD AND APPARATUS FOR CALIBRATING MEDICAL IMAGE DATA

BACKGROUND OF THE INVENTION

1. Field of the Invention

The present invention is directed to a method and apparatus for calibrating image data from a given medical imaging protocol.

2. Description of the Prior Art

In the medical imaging field, several imaging schemes are known. For example PET (Positron Emission Tomography) is a method for imaging a subject in 3D using an injected radioactive substance which is processed in the body, typically resulting in an image indicating one or more biological functions.

The Standardized Uptake Value (SUV) is a widely-used measure for quantifying radiotracer (especially 18F-FDG) uptake in clinical PET scans. This value is computed from the number of counts of emission events recorded per voxel in the image reconstructed from the event data captured in the PET scan (coincidence emission events along the line of response). Its use is intended to provide normalization for differences in patient size and body composition, along with the dose of radiotracer injected, thereby enabling inter-study comparison, both between and within individual patients.

While differences in body composition and injected dose represent one source of variation, differences in scanner hardware and reconstruction represent another, and these are not addressed by the use of SUV. These unaddressed sources of variation impede the acceptance of PET as a quantitative imaging tool for lesion characterization, prognostic stratification and treatment monitoring, since differences in scanner hardware and reconstruction can significantly impact generated SUV. For example, SUVs typically increase with the number of iterations performed for iterative reconstruction techniques such as OSEM. Also, post-reconstruction smoothing will reduce SUVs in areas of high uptake. As such, better standardization and improved comparability between scanners and reconstruction protocols are required.

A number of review articles addressing the issue of standardization have been published in recent years, and in general, fall into one of three categories:

1. The EORTC (Young et al., 1999, Measurement of clinical and subclinical tumor response using [18F]-FDG and PET: Review and 1999 EORTC recommendations, Eur J Can. 35 (13) 1773-1782), NCI (Shanker et al., 2006, Consensus recommendation for the use of 18F-FDG as an indicator of therapeutic response in patients in National Cancer Institute trials, JNM. 47 (6) 1059-1066) and SNM (Delbeke et al., 2006, Procedure guideline for tumor imaging with 18F-FDG PET/CT 1.0, JNM. 47 (5) 885-895) provide no specific recommendations for normalizing the effect of reconstruction or scanner hardware on SUV. Instead, they focus on standardizing the imaging procedure (i.e., interval between injection and acquisition, cross-calibration of dose counters, etc.).
2. The so called "Netherlands Protocol" (Boellaard et al., 2008, The Netherlands protocol for standardization and quantification of FDG whole body PET studies in multi-centre trials, Eur J Nuc Med Mol Imaging. 35 (12) 2320-2333) provides a very prescriptive protocol with a specific set of reconstruction parameters for one scanner from each of the main manufacturers, along with upper and lower bounds for the recovery coefficients expected with a modified NEMA Image Quality phantom. An updated version of these guidelines was recently published by Boellaard et al., (2010, FDG PET and PET/CT: EANM procedure guidelines for tumor PET imaging: version 1.0, Eur J Nuc Med Mol Imaging. 37, 181-200).
3. Weber et al. (2007, Monitoring cancer treatment with PET/CT: Does it make a difference?, JNM. 48 (1) 36S-44S) suggests providing only bounds for SUV measures on a given (i.e., NEMA-like) phantom rather than specifying reconstruction parameters.

The third alternative may be the most appealing from a manufacturer's perspective, since it offers the greatest flexibility, allowing the manufacturer to take the decision on the most suitable reconstruction configuration. However, this proposal would still require all manufacturers to reconstruct and display their images to conform to the lowest common denominator, removing any competitive advantages.

There is currently no apparent solution built by a hardware or a software manufacturer beyond these recommendations from the clinical literature.

While not addressing the issue of reconstruction-dependent variation in SUV, a variety of corrections for SUV are clinically used to correct for body composition and blood glucose concentration. These corrections incorporate patient measurements (e.g., height, weight, blood glucose concentration) and adjust the standard body-weight normalized SUV as a function of these patient-specific parameters.

SUMMARY OF THE INVENTION

An object of the present invention is to address the aforementioned problems and provide improvements upon the known devices and methods.

In general terms, one embodiment of a first aspect of the invention is a method of calibrating image data from a given medical imaging protocol, including obtaining reference image data from a scan of a reference object using the medical imaging protocol, comparing the obtained reference image data of the reference object to standard reference image data for the reference object, and modifying the obtained reference image data to reduce an error between the obtained reference image data and the standard reference image data.

This allows image data from any medical imaging protocol to be easily calibrated or checked against a standard for that image data. This could be a globally or regionally agreed standard for the image data, allowing repetition of results across different medical imaging protocols, such as different scanner types, or different methods of reconstruction.

Preferably, the method further includes obtaining subject image data from a scan of a subject using the medical imaging protocol, and modifying the subject image data based on the modified reference image data.

Thus an image captured and/or reconstructed by the given protocol can be adjusted to agree with the standard image data.

More preferably, the method further includes obtaining from the modified subject image data a value of a variable for display with unmodified subject image data.

This allows the local protocol to be used for visualization, and the calibrated data to be used for quantification for the same image data.

Suitably, the reference object is a phantom comprising at least one portion containing a radiopharmaceutical substance. In an embodiment, the portion is a sphere.

In one embodiment, the obtained reference image data is an obtained image of the phantom, the standard reference image data is a standard image of the phantom, and the step of comparing comprises comparing respective features of the obtained and standard images.

In this embodiment, the step of comparing respective features comprises: comparing a sphere-to-background ratio of the obtained image with a sphere-to-background ratio for the standard image; and determining an error between the respective sphere-to-background ratios.

Suitably, the step of comparing respective features comprises comparing the sphere-to-background ratio of the obtained image with a range for the sphere-to-background ratio for the standard image, the range having upper and lower bounds.

In an embodiment, the step of modifying comprises an iterative process comprising the steps of: filtering the obtained reference image data by a given amount; comparing the filtered image data with the standard reference image data; and altering the amount of filtering.

Suitably, the step of filtering comprises convolving the obtained reference image data with an image filter variable according to a given factor.

Preferably, the image filter is a Gaussian filter, and the factor is the full width at half maximum of the Gaussian filter.

In an embodiment, the method further includes recording the given amount or factor for the respective given medical imaging protocol.

In one embodiment, the step of modifying the subject image data includes modifying the subject image data by the recorded amount or factor for the given imaging protocol.

Suitably, the step of obtaining a value of a variable for display includes obtaining an SUV value from the modified subject image data.

In a preferred embodiment, the method further includes identifying a region of interest in the unmodified subject image data, identifying the corresponding region in the modified subject image data; and obtaining the value for display from the corresponding region in the modified subject image data.

This allows the quantification to be concentrated on a region of interest, which may be selected by a user.

Suitably, one or more of the following steps is steps performed for the region of interest only: obtaining the reference image data from the scan of the reference object, comparing the obtained reference image data of the reference object to standard reference image data for the reference object, modifying the obtained reference image data to reduce an error between the obtained reference image data and the standard reference image data, and modifying the subject image data based on the modified reference image data.

One embodiment of a second aspect of the invention is a method of calibrating image data from a given medical imaging protocol, including obtaining subject image data from a scan of a subject using the medical imaging protocol, modifying the subject image data using a modifier based on reference image data captured using the same medical imaging protocol, and obtaining from the modified subject image data a value of a variable for display with unmodified subject image data.

This allows an image captured and/or reconstructed by the given protocol to be adjusted to agree with the reference image data for that given protocol.

Preferably, the reference image data comprises image data of a reference object modified to reduce an error in comparison to standard reference image data of the reference object.

One embodiment of a third aspect of the invention is an apparatus for calibrating image data from a given medical imaging protocol, captured by an imaging apparatus, including a processor, configured to obtain reference image data from a scan of a reference object using the medical imaging protocol, and to compare the obtained reference image data of the reference object to standard reference image data for the reference object, and to modify the obtained reference image data to reduce an error between the obtained reference image data and the standard reference image data.

One embodiment of a fourth aspect of the invention is an apparatus for calibrating image data from a given medical imaging protocol, captured by an imaging apparatus, including a processor configured to obtain subject image data from a scan of a subject using the medical imaging protocol, and to modify the subject image data based on reference image data captured using the same medical imaging protocol, and to obtain from the modified subject image data a value of a variable for display with unmodified subject image data. The apparatus also includes a display device that displays unmodified image data with the value.

One embodiment of a fifth aspect of the invention is a non-transitory computer-readable storage medium storing computer program code that, when loaded into or run on a computer, causes the computer to become apparatus, or to implement a method according to any of the above described aspects or embodiments.

DESCRIPTION OF THE PREFERRED EMBODIMENTS

When the following terms are used herein, the accompanying definitions can be applied:
FWHM Full width at half maximum
NEMA National Electrical Manufacturers Association
PET Positron Emission Tomography
ROI Region Of Interest
SBR Sphere-to-Background Ratio
SUV Standardized Uptake Value
SUVref SUV Reference This invention is concerned with validating a given imaging protocol and/or reconstruction against a standard, and using this information to help interpret an image from the given protocol/reconstruction. It is applicable to a variety of reconstruction protocols (e.g. for different imaging modalities, such as PET, SPECT; for different reconstruction algorithms, such as OSEM).

This allows the manufacturer to display the image optimally-reconstructed for clinical use, whilst quantifying from a non-displayed, processed image that is known to produce SUVs within globally-agreed bounds for a specified phantom.

Embodiments generally calibrate a given protocol against standard data, using for example a phantom, and use the calibration to modify data captured using the protocol, so that the modified data can be used, for example, for quantification alongside the viewed image.

In summary, embodiments of the invention describe ways to process an image to produce uptake values that are consistent within certain limits throughout a series of possible variants (scanner, reconstruction protocol, etc).

Figure 1:
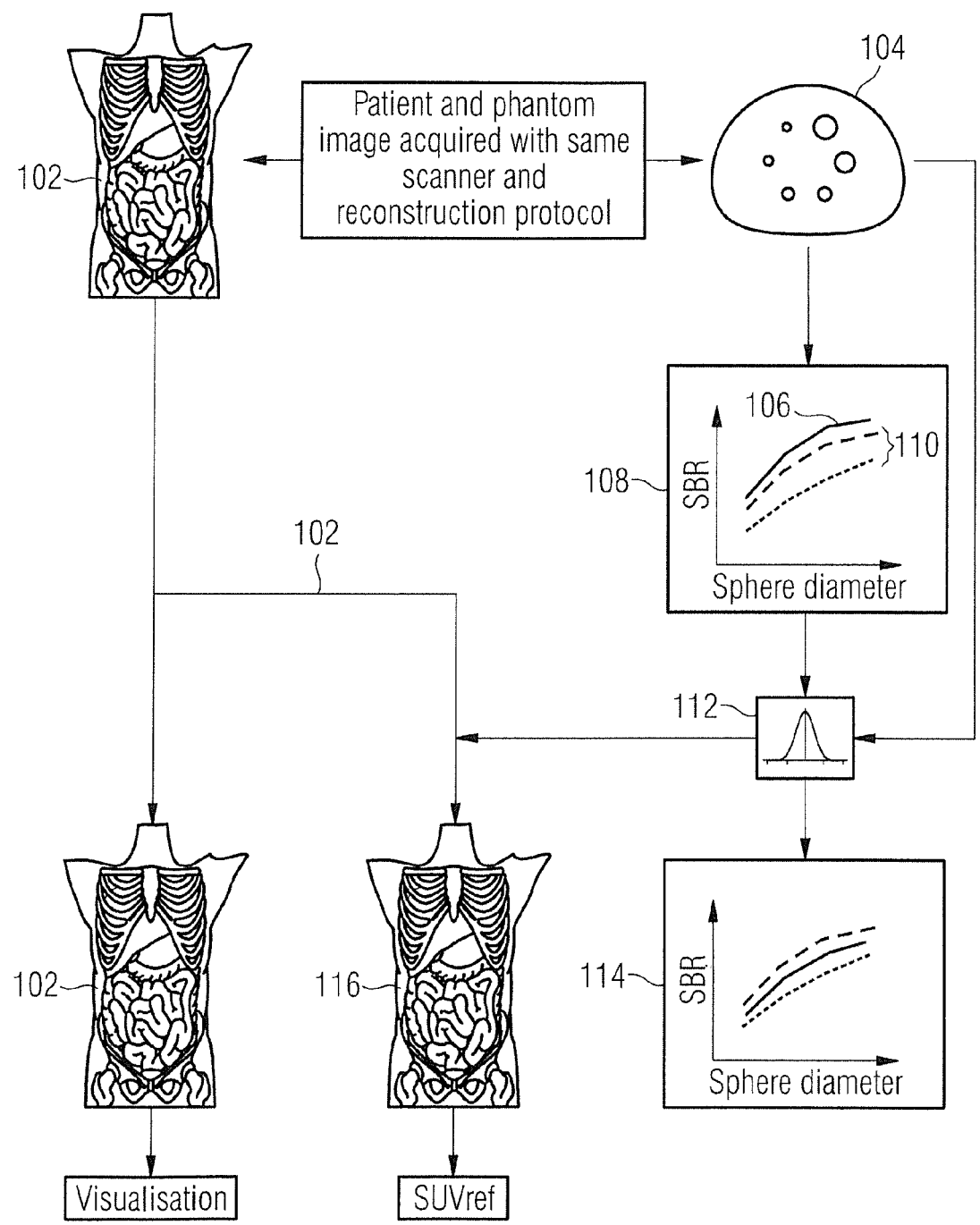
FIG. 1 is a diagram illustrating typical steps of a method according to an embodiment of the invention.

FIG. 1 Illustrates the typical steps involved in an embodiment of the invention. The scanner and reconstruction protocol used to generate patient image 102 is also applied to a phantom, producing phantom image 104 from this specific protocol. The sphere-to-background ratio (SBR) is measured for the phantom image 104, and is shown as the solid line (106) in graph 108. This SBR measurement (106) is compared to standard bounds (dotted lines 110) for the SBR for an image of the phantom being used. These standard bounds are the reference point for any protocol being tested or calibrated in this way.

A filter size (filter 112) is selected that when applied to the phantom image from the given protocol produces measured SBR within the standard bounds 110, as shown in graph 114. This filter size is then used in applying the filter 112 to the patient image 102 to produce a filtered clinical image 116 used for quantification. The original clinical image 102 is used for visualization, with any regions of interest drawn on this image propagated to the filtered image (116) for computation of the quantification required for that region. The value returned in this case is labeled as SUVref—a standardized measurement of the SUV—which can then be presented alongside the image reconstructed as per the given protocol, or overlaid on the image.

In a specific embodiment, a reference SUV (SUVref) is computed from an image as follows:
1. A region of interest (ROI) is drawn on the clinical image of interest that has been reconstructed as desired by the clinician or physicist.
2. This ROI is propagated to an unshown copy of the clinical image that has been convolved with a 3D Gaussian filter. The full width at half maximum (FWHM) of this filter is specific to the reconstruction protocol used for the image and is computed as described below. The FWHM of the filter to be used to this reconstruction could, for example, be stored in the DICOM header or in a pre-populated look-up table.
3. The maximum SUV within the propagated ROI is calculated and returned to the clinician as the SUVref, in addition to the typical quantification values obtained from the original image.

The FWHM of the filter applied to an image reconstructed with a certain protocol is computed so as to produce SUV measures for a phantom (e.g., a NEMA Image Quality Phantom) within a fixed set of globally-agreed bounds.

One approach to computing the filter FWHM for a given clinical reconstruction protocol is to use an acquired NEMA Image Quality phantom, reconstructed with the same protocol. One embodiment of the process is as follows:
1. Reconstruct acquired NEMA Image Quality phantom with desired clinical reconstruction protocol.
2. For each 18F-filled hot sphere, measure the sphere-to-background ratio (SBR) by dividing the maximum voxel intensity within a hot sphere by the mean background intensity.
3. Compare the SBRs measured for this reconstruction to a globally-agreed standard. One approach for determining a globally-agreed standard is described below.
4. Repeat steps 2 and 3, following convolution of the reconstructed image with a 3D Gaussian filter with increasing FWHM, until the difference between the measured SBRs and those for the globally-agreed standard is minimized.

A globally-agreed standard set of SBRs could be determined by taking a diverse set of reconstructions, and optimizing the FWHM of the filters applied to each, so as to minimize the variance between the measured SBRs for this set of reconstruction. An alternative would be to use a set of SBRs recommended by a published guideline (e.g., Boellaard et al., 2010).

To investigate the feasibility of embodiments of this invention an acquired NEMA Image Quality phantom was reconstructed with a diverse set of 11 reconstruction protocols. These were then used to validate the procedure detailed above for determining a globally-agreed set of SBRs. A set of filters ranging from 0 mm to 6 mm were selected to reduce the mean variation between measured SBRs from 0.83 to 0.04 (see FIG. 2).

Figure 2:
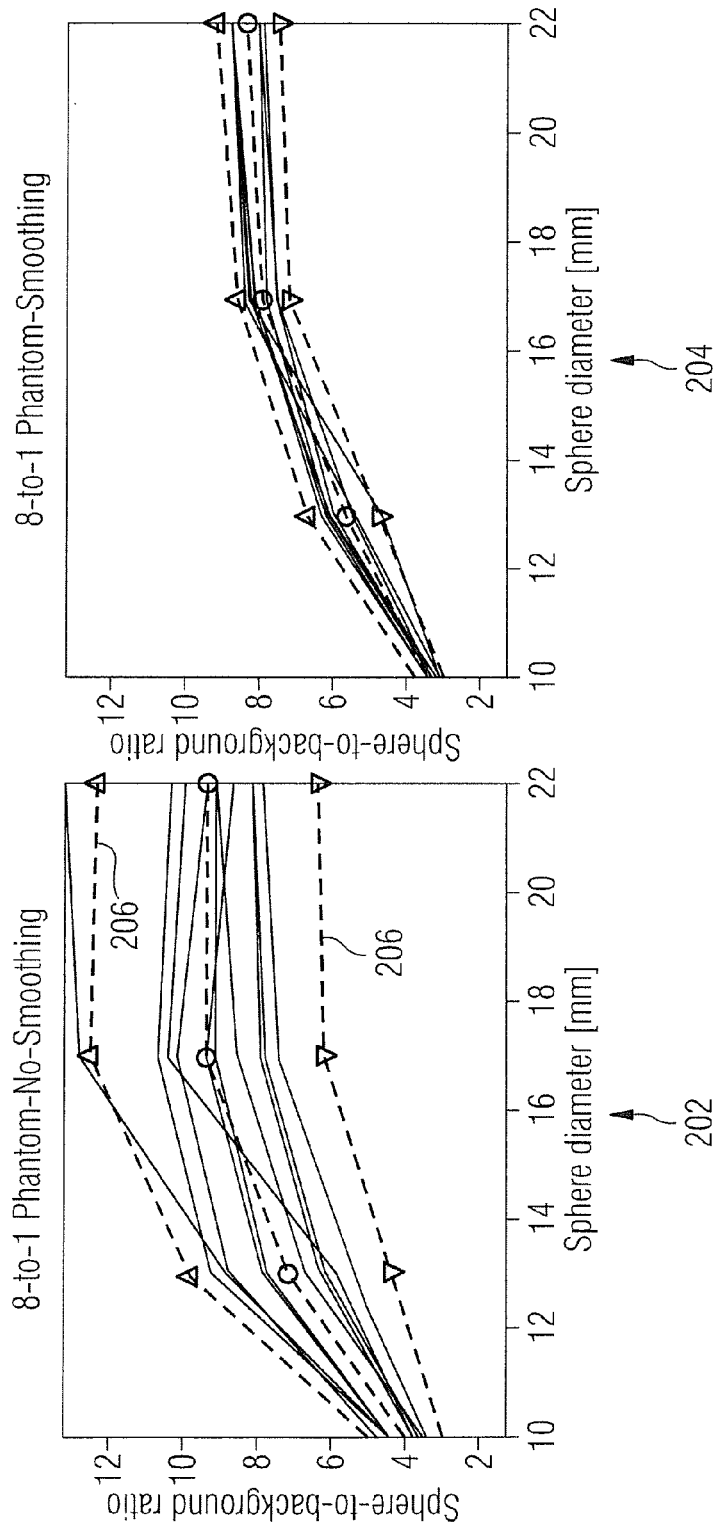
FIG. 2 is a diagram illustrating comparison of phantom SBRs according to an embodiment of the invention.

FIG. 2 shows the sphere-to-background ratios (SBRs) for the set of reconstructions of the NEMA Image Quality phantom. Dashed lines 206 in the first graph (204) indicate the mean+/−2 standard deviations in the pre-filtered SBRs. Application of the selected filters reduces the variance in the measured SBRs, as shown in the second graph (204).

To investigate the feasibility of applying these phantom-optimized filters to clinical data, the NEMA phantom was reconstructed with two additional reconstructions, and filters FWHMs selected for these reconstructions. The reconstructions were selected so as to minimize the difference between the measured SBRs and the mean SBRs produced following filtering of the diverse set of reconstructions shown in FIG. 2 (right side plot 204). These filters were then applied to clinical images reconstructed with the same pair of reconstructions. For a set of 60 ROIs corresponding to various anatomical features in 6 clinical scans, the mean percentage difference in SUV was reduced from 49.0% (+/−2.1) to 5.0% (+/−1.0) with SUVref, over a set of 60 ROIs in various body regions from 6 patient scans.

In an alternative embodiment of this invention, as opposed to filtering the entire image prior in order to compute SUVref measurements, a smaller region encompassing the ROI can instead be filtered. In this case, the filtered image used for quantification (116 in FIG. 1) is of the ROI only.

In another embodiment, a non-Gaussian (potentially, spatially non-uniform) filter can be used. This may better-reflect the effects of differences in reconstruction on measured SUV. The image can also be processed using techniques other than filtering: the key element of the processing is to combine neighboring uptake values. For example, a basic blurring effect, incorporating uptake values from neighboring voxels, may be used.

In other embodiments, the NEMA-IQ phantom can be used for the calibration in a different way (with different ratios of activity in the spheres). Alternative phantoms can be used to compute the appropriate FWHM of the Gaussian filter used for a given reconstruction protocol.

In another embodiment, additional constraints may be considered when determining the globally-agreed bounds for the measure SBRs. For example, an additional requirement may be to maintain the ability to distinguish between regions of different intensity. This prevents excessive smoothing following selection of large FWHM. Too much smoothing produces results which are much less clinically useful—if the image for quantification contains little detail, the values derived from it will not be of use.

Figure 3:
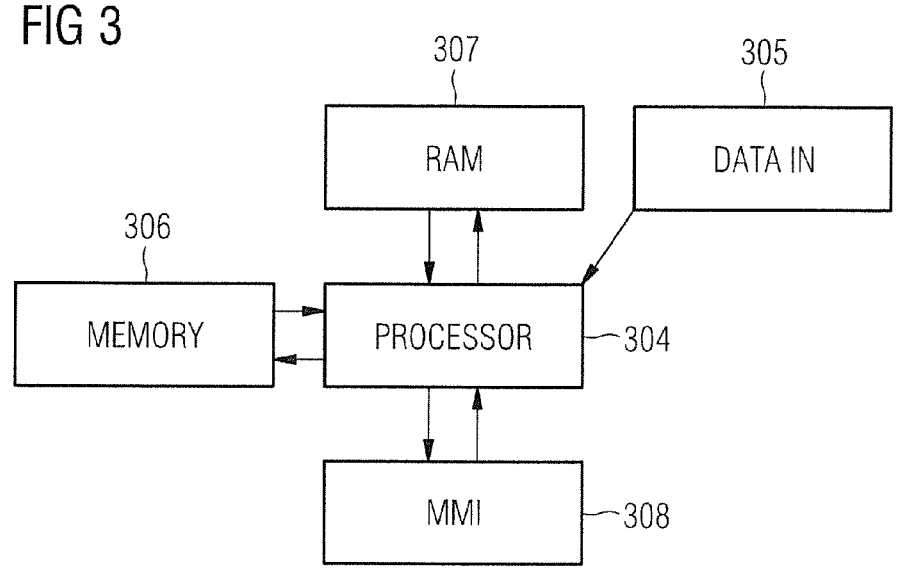
FIG. 3 is a diagram illustrating an apparatus according to an embodiment of the invention.

Referring to FIG. 3, the above embodiments of the invention may be conveniently realized as a computer system suitably programmed with instructions for carrying out the steps of the methods according to the invention.

For example, a central processing unit 304 is able to receive data representative of medical scans via a port 305 which could be a reader for portable data storage media (e.g. CD-ROM); a direct link with apparatus such as a medical scanner (not shown) or a connection to a network.

Software applications loaded on memory 306 are executed to process the image data in random access memory 307.

The processor 304 in conjunction with the software can perform the steps such as comparing phantom images with the standard, modifying the received patient image data based on a given FWHM, etc.

A Man-Machine interface 308 typically includes a keyboard/mouse/screen combination (which allows user input such as initiation of applications) and a screen on which the results of executing the applications are displayed.

It will be appreciated by those skilled in the art that the invention has been described by way of example only, and that a variety of alternative approaches may be adopted without departing from the scope of the invention, as defined by the appended claims.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of calibrating image data obtained using a medical imaging protocol, comprising:
   providing a processor with reference image data from a scan of a reference object using the medical imaging protocol;
   in said processor, comparing the obtained reference image data of the reference object to standard reference image data for the reference object to obtain a comparison result that indicates a degree of deviation of said reference image data with respect to said standard reference image data;
   in said processor, using said comparison result to set a parameter of a filter that, when applied to filter said reference image data, reduces said degree of deviation so to be within a predetermined range;
   providing said processor also with subject image data obtained from a scan of subject using the medical imaging protocol, said subject image data comprising at least one visually under-represented part of said subject;
   in said processor, filtering the subject image data with said filter to obtain filtered obtained filter subject image data;
   maintaining a set of said subject image data without filtering thereof, as unfiltered subject image data, and making only said unfiltered subject image data, and not said filtered subject image data, available at an output of said processor as a data file in a form allowing display of an image of said subject corresponding to said unfiltered image data; and
   in said processor, obtaining a value for a variable from said filtered subject image data that represents said degree of under representation of said at least one part of said subject in said unfiltered subject image data, and including an electronic representation of said variable in said data file that contains said unfiltered subject image data for display with said display of said image of said subject corresponding to said unfiltered image data.

2. A method according to claim 1, wherein the step of obtaining a value of a variable for display comprises obtaining an SUV value from the filtered subject image data.

3. A method according to claim 1, further comprising:
   identifying a region of interest in the unfiltered subject image data;
   identifying the corresponding region in the filtered subject image data that corresponds to the identified region of interest; and
   obtaining the value for display from the corresponding region in the filtered subject image data.

4. A method according to claim 3, comprising performing one or more of the following steps for the region of interest only: obtaining the reference image data from the scan of the reference object; comparing the obtained reference image data of the reference object to standard reference image data for the reference object; filtering the obtained reference image data to reduce an error between the obtained reference image data and the standard reference image data; and filtering the subject image data based on the filtered reference image data.

5. A method according to claim 1, comprising employing, as said reference object, a phantom comprising at least one portion containing a radiopharmaceutical substance.

6. A method according to claim 5, wherein the portion is a sphere.

7. A method according to claim 5, wherein the obtained reference image data is an obtained image of the phantom, and wherein the standard reference image data is a standard image of the phantom,
   and wherein the step of comparing comprises comparing respective features of the obtained and standard images.

8. A method according to claim 7, wherein the step of comparing respective features comprises:
   comparing a sphere-to-background ratio of the obtained image with a sphere-to-background ratio for the standard image; and
   determining an error between the respective sphere-to-background ratios.

9. A method according to claim 8, wherein the step of comparing respective features comprises comparing the sphere-to-background ratio of the obtained image with a range for the sphere-to-background ratio for the standard image, the range having upper and lower bounds.

10. A method according to claim 1, wherein said comparing of the obtained reference image of the reference object to standard reference image data for the reference object, and using said comparison result to set a parameter of a filter, are repeated in an iterative process comprising the steps of:
    filtering the obtained reference image data by a given amount;
    implementing said comparing of the filtered image data with the standard reference image data to obtain said comparison result; and
    altering the amount of filtering dependent on said comparison result.

11. A method according to claim 10, wherein the step of filtering comprises convolving the obtained reference image data with an image filter variable according to a given factor.

12. A method according to claim 11, wherein the image filter is a Gaussian filter, and the factor is the full width at half maximum of the Gaussian filter.

13. A method according to claim 10, further comprising recording the given amount or factor for the respective given medical imaging protocol.

14. An apparatus for calibrating image data from a given medical imaging protocol, said apparatus comprising:
    a processor having an input provided with reference image data from a scan of a reference object using the medical imaging protocol;
    said processor being configured to compare the obtained reference image data of the reference object to standard reference image data for the reference object to obtain a comparison result that indicates a degree of deviation of said reference image data with respect to said standard reference image data;
    said processor being configured to using said comparison result to set a parameter of a filter that, when applied to filter said reference image data, reduces said degree of deviation so to be within a predetermined range;

said processor also being provided with subject image data obtained from a scan of subject using the medical imaging protocol, said subject image data comprising at least one visually under-represented part of said subject;

said processor being configured to filter the subject image data with said filter to obtain filtered subject image data said processor being configured to maintain a set of said subject image data without filtering thereof, as unfiltered subject image data, to make only said unfiltered subject image data, and not said filtered subject image data, available at an output of said processor as a data file in a form allowing display of an image of said subject corresponding to said unfiltered image data; and said processor being configured to obtain a value for a variable from said filtered subject image data that represents said degree of under representation of said at least one part of said subject in said unfiltered subject image data, to include an electronic representation of said variable in said data file that contains said unfiltered subject image data for display with said display of said image of said subject corresponding to said unfiltered image data.

15. An apparatus according to claim 14, comprising a display unit in communication with said processor, to which said processor is configured to supply said data file, in order to display, at said display unit, said image of said subject corresponding to said unfiltered image data and said representation of said variable.

16. A non-transitory, computer-readable data storage medium encoded with programming instructions, said data storage medium being loaded into a computerized processor and said programming instructions causing said processor to:

receive reference image data obtained from a scan of a reference object using a medical imaging protocol;

compare the obtained reference image data of the reference object to standard reference image data for the reference object to obtain a comparison result that indicates a degree of deviation of said reference image data with respect to said standard reference image data;

use said comparison result to set a parameter of a filter that, when applied to filter said reference image data, reduces said degree of deviation so to be within a predetermined range;

also receive with subject image data obtained from a scan of subject using the medical imaging protocol, said subject image data comprising at least one visually under-represented part of said subject;

filter the subject image data with said filter to obtain filtered subject image data;

maintain a set of said subject image data without filtering thereof, as unfiltered subject image data, and make only said unfiltered subject image data, and not said filtered subject image data, available at an output of said processor as a data file in a form allowing display of an image of said subject corresponding to said unfiltered image data; and obtain a value for a variable from said filtered subject image data that represents said degree of under representation of said at least one part of said subject in said unfiltered subject image data, and include an electronic representation of said variable in said data file that contains said unfiltered subject image data for display with said display of said image of said subject corresponding to said unfiltered image data.

* * * * *